(12) United States Patent
Luongo et al.

(10) Patent No.: US 10,238,989 B2
(45) Date of Patent: Mar. 26, 2019

(54) HYBRID GRADIENT DELIVERY SYSTEM AND OPERATION

(71) Applicant: Waters Technologies Corporation, Milford, MA (US)

(72) Inventors: Joseph A. Luongo, Walpole, MA (US); Craig Hamilton Dobbs, Mendon, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 855 days.

(21) Appl. No.: 14/364,148

(22) PCT Filed: Dec. 7, 2012

(86) PCT No.: PCT/US2012/068520
§ 371 (c)(1),
(2) Date: Jun. 10, 2014

(87) PCT Pub. No.: WO2013/090147
PCT Pub. Date: Jun. 20, 2013

(65) Prior Publication Data
US 2014/0367319 A1    Dec. 18, 2014

Related U.S. Application Data

(60) Provisional application No. 61/570,446, filed on Dec. 14, 2011.

(51) Int. Cl.
*B01D 15/14* (2006.01)
*G01N 30/34* (2006.01)
(Continued)

(52) U.S. Cl.
CPC .......... *B01D 15/14* (2013.01); *B01D 15/166* (2013.01); *G01N 30/34* (2013.01); *G01N 30/20* (2013.01);
(Continued)

(58) Field of Classification Search
None
See application file for complete search history.

(56) References Cited

U.S. PATENT DOCUMENTS

| 4,310,420 A | 1/1982 | Konishi et al. |
| 4,437,812 A | 3/1984 | Abu-Shumays et al. |

(Continued)

FOREIGN PATENT DOCUMENTS

| EP | 0467665 A2 | 1/1992 |
| JP | 57190463 U | 12/1982 |

(Continued)

OTHER PUBLICATIONS

International Search Report & Written Opinion in International Patent Application No. PCT/US12/68520, dated Feb. 22, 2013; 8 pages.

(Continued)

*Primary Examiner* — Kara M Peo
(74) *Attorney, Agent, or Firm* — Schmeiser, Olsen & Watts LLP

(57) ABSTRACT

A liquid chromatography system includes a gradient proportioning valve in fluidic communication with sources of solvent. From the solvent sources, the gradient proportioning valve produces a low-pressure gradient stream. A first pump is in fluidic communication with the gradient proportioning valve to receive, pressurize, and move the pressurized low-pressure gradient stream to a flow-combining device. A second pump operates in parallel with the first pump and moves a pressurized solvent stream to the flow-combining device where the pressurized solvent stream combines with the low-pressure gradient stream to produce a high-pressure gradient stream. A second gradient proportioning valve can produce, from a second plurality of sources of solvent, a second low-pressure gradient stream, wherein the solvent stream moved by the second pump to the (Continued)

flow-combining device and combined with the other low-pressure gradient stream comprises the second low-pressure gradient stream.

6 Claims, 3 Drawing Sheets

(51) Int. Cl.
*B01D 15/16* (2006.01)
*G01N 30/20* (2006.01)
*G01N 30/38* (2006.01)

(52) U.S. Cl.
CPC ......... *G01N 30/38* (2013.01); *Y10T 137/0363* (2015.04); *Y10T 137/85986* (2015.04)

(56) References Cited

U.S. PATENT DOCUMENTS

| 4,981,597 | A | 1/1991 | Allington et al. |
| 5,630,706 | A | 5/1997 | Yang |
| 5,862,832 | A | 1/1999 | Victor et al. |
| 2010/0065495 | A1 | 3/2010 | Shreve et al. |
| 2011/0209766 | A1 | 9/2011 | Witt et al. |

FOREIGN PATENT DOCUMENTS

| JP | 62266459 A | 11/1987 |
| JP | 2000356629 A | 12/2000 |
| JP | 2004138413 A | 5/2004 |
| WO | 2010030723 A1 | 3/2010 |
| WO | 2010068273 A1 | 6/2010 |
| WO | 2011085353 A1 | 7/2011 |

OTHER PUBLICATIONS

Web page: http://www.shimadzu.com/an/x2-6.html, titled, "Nexera X2 Ultimate Flexibility", visited on Dec. 11, 2012, 2 pages.
Notice of Rejection in counterpart Japanese Patent Application No. 2014-547318, dated Oct. 18, 2016; 9 pages.
International Preliminary Report on Patentability in International Patent Application No. PCT/US12/68520, dated Jan. 28, 2016; 7 pages.
Extended Search Report in European Patent Application No. 12858173.3, dated Dec. 22, 2016; 7 pages.
Examination Report in European Patent Application No. 12858173.3, dated Jul. 18, 2017; 5 pages.

HYBRID GRADIENT DELIVERY SYSTEM AND OPERATION

RELATED APPLICATION

This application claims the benefit of and priority to co-pending U.S. provisional application No. 61/570,446, filed Dec. 14, 2011, titled "Hybrid Gradient Delivery System and Operation," the entirety of which is incorporated by reference herein.

FIELD OF THE INVENTION

The invention relates generally to liquid chromatography systems. More specifically, the invention relates to hybrid gradient delivery systems that combine aspects of high-pressure gradient systems and low-pressure gradient systems.

BACKGROUND

Chromatography is a set of techniques for separating a mixture into its constituents. In liquid chromatography systems, generally, one or more high-pressure pumps take in solvents and deliver a liquid solvent composition to a sample manager, where a sample awaits injection into the mixture. The sample is the material under analysis, examples of which include complex mixtures of proteins, protein precursors, protein fragments, reaction products, and other compounds, to list but a few. From the sample manager, the resulting liquid composition, comprised of the mixture of solvents and injected sample, moves to a point of use, such as a column of particulate matter. By passing the composition through the column, the various constituents in the sample separate from each other at different rates and thus elute from the column at different times. A detector receives the elution from the column and produces an output from which the identity and quantity of the analytes may be determined.

High-performance liquid chromatography (HPLC) uses two basic elution modes: isocratic elution and gradient elution. In the isocratic elution mode, the mobile phase, comprised of either a pure solvent or a mixture of solvents, remains the same throughout the chromatography run. In the gradient elution mode, the composition of the mobile phase changes during the separation. Creation of the gradient (i.e., changing mobile phase composition) entails the mixing of multiple solvents, the proportions of which change over time in accordance with a predetermined timetable. Some HPLC systems create the gradient under high pressure, by mixing the solvents downstream of the pumps. Such HPLC systems are also referred to herein as high-pressure gradient systems. Other HPLC systems create the gradient under low pressure, using a gradient proportioning valve to select from up to four solvents, mixing the multiple solvents in front of a single aspirating pump, and changing the proportions of the solvents over time. Such HPLC systems are also referred to herein as low-pressure gradient systems.

The decision between a high-pressure and a low-pressure gradient system involves a variety of tradeoffs, only a few of which are mentioned here. For one, high-pressure gradient systems have lesser dwell volumes than low-pressure gradient systems because the solvent mixing occurs after the pumps instead of before the intake side of the pump. However, because of the location of mixing, low-pressure gradient systems can produce a gradient with just one pump, whereas high-pressure gradient systems generally require one pump for each solvent. Hence, low-pressure gradient systems are more amenable than high-pressure gradient systems to tertiary and quaternary gradients, and are thus predominantly used for such chromatography applications, whereas high-pressure gradient systems are generally used for binary gradients.

Often, however, it is desirable to blend more than two solvents in a gradient, with a third solvent being a modifier, such as TFA (triflouroacetic acid), introduced at a constant percentage. Furthermore, it is easier to blend in a more concentrated mixture of the modifier to the total composition than to add the modifier to each of the other solvents at the desired lower concentration. For example, if 0.1% TFA is the desired concentration, it is much easier to produce a 1% concentration of TFA, and introduce it in 10% proportion to the other two solvents, than to mix a 0.1% concentration of TFA in each of the other two solvents. Hence, a low-pressure gradient system is generally used for chromatography runs to introduce the third modifier solvent instead of a high-pressure gradient system. Use of the low-pressure gradient system for this purpose, though, has disadvantages of an increased dwell volume (in comparison to a high-pressure gradient system) and limiting the maximum percentage of one of the two other solvents to 90%.

SUMMARY

In one aspect, the invention features a solvent delivery system for use in a liquid chromatography system. The solvent delivery system comprises a gradient proportioning valve in fluidic communication with a plurality of sources of solvent and producing therefrom a low-pressure gradient stream. A first pump is in fluidic communication with the gradient proportioning valve to receive and pressurize the low-pressure gradient stream and to move the pressurized low-pressure gradient stream to a flow-combining device. A second pump operates in parallel with the first pump. The second pump moves a pressurized solvent stream to the flow-combining device where the pressurized solvent stream combines with the pressurized low-pressure gradient stream to produce a high-pressure gradient stream.

In another aspect, the invention features a method for blending solvents in a liquid chromatography system. A low-pressure gradient stream is produced from a plurality of sources of solvent, pressurized, and moved to a flow-combining device while a pressurized solvent stream is moved to the flow-combining device. At the flow-combining device, the pressurized solvent stream mixes with the pressurized low-pressure gradient stream to produce a high-pressure gradient stream.

In still another aspect, the invention features a liquid chromatography system comprising a solvent delivery system. The solvent delivery system includes a gradient proportioning valve in fluidic communication with a plurality of sources of solvent, producing therefrom a low-pressure gradient stream. A first pump is in fluidic communication with the gradient proportioning valve to receive and pressurize the low-pressure gradient stream and to move the pressurized low-pressure gradient stream to a flow-combining device. A second pump operates in parallel with the first pump. The second pump moves a pressurized solvent stream to the flow-combining device where the pressurized solvent stream combines with the pressurized low-pressure gradient stream to produce a high-pressure gradient stream.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Solvent delivery systems described herein can be deemed hybrid systems because they combine features of a high-pressure gradient system with those of a low-pressure gradient system. As a hybrid, the solvent delivery systems function primarily as binary gradient systems having minimized dwell volume and flexibility for solvent selection.

Figure 1:
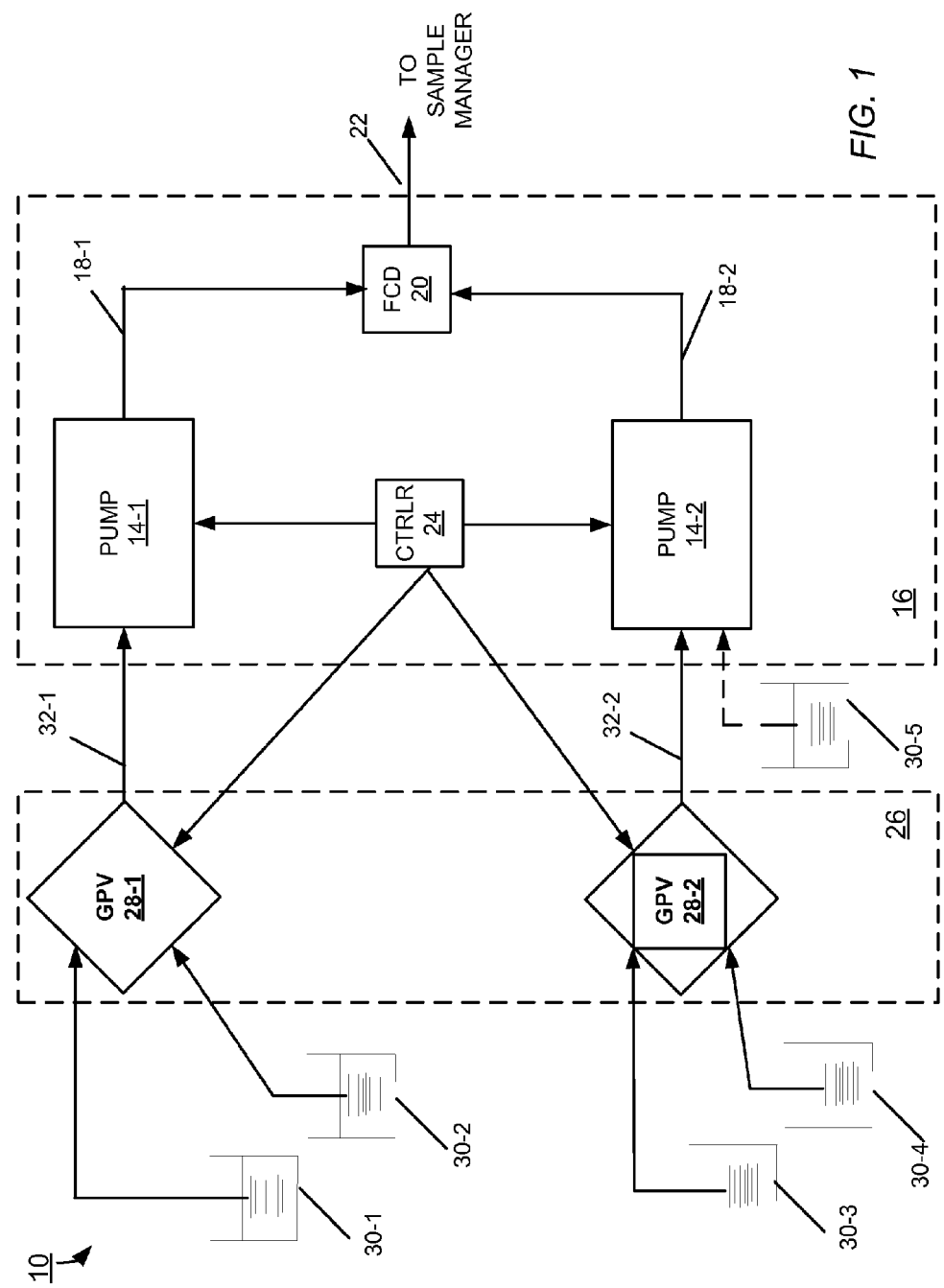
FIG. 1 is a functional block diagram of an embodiment of a hybrid solvent delivery system for a liquid chromatography system, the hybrid solvent delivery system combining features of a high-pressure gradient system and a low-pressure gradient system.

FIG. 1 shows an embodiment of a hybrid solvent delivery system 10 for producing and moving a solvent composition to a sample manager (not shown), also known as an autosampler, where a sample is introduced to the solvent composition. The features of a high-pressure gradient system adapted for use by the hybrid solvent delivery system 10, outlined by dashed box 16, include two pumps 14-1, 14-2 (generally, 14) operating in parallel. In brief overview, each pump 14-1, 14-2 includes a primary pumping actuator and an accumulator pumping actuator coupled in series. The pumps 14 can be of the type used in the 2545 Binary Gradient Module manufactured by Waters Corporation of Milford, Mass.

The outlets of the pump 14-1, 14-2 are connected at the same or substantially the same mechanical location, here represented as a flow-combining device (FCD) 20. Example implementations of the flow-combining device 20 include, but are not limited to, a T-section and a mixer. Each pump 14-1, 14-2 moves a solvent stream 18-1, 18-2, respectively, at high pressure, to this flow-combining device 20, where the pressurized solvent streams 18-1, 18-2 combine to produce a pressurized solvent composition 22 that is delivered over time to the sample manager. A gradient controller 24 is in communication with the pumps 14 to manage the speed of each pump 14 in order to deliver more or less of each solvent stream 18-1, 18-2 over the course of the separation.

The features of the hybrid solvent delivery system 10 adapted from a low-pressure gradient system are shown within dashed box 26 and include two gradient proportioning valves (GPV) 28-1, 28-2 (generally, 28) operating in parallel. Each GPV 28 is in fluidic communication with up to four solvent reservoirs 30 (here, only two reservoirs per GPV are shown; the GPV 28-1 is in fluidic communication with solvent reservoirs 30-1, 30-2; and the GPV 28-2 is in fluidic communication with solvent reservoirs 30-3, 30-4). In addition, each GPV 28 is in fluidic communication with one of the pumps 14; the pump 14-1 acquires the low-pressure gradient stream 32-1 from the GPV 28-1, and the pump 14-2 acquires the low-pressure gradient stream 32-2 from GPV 28-2.

Each GPV 28 includes an inlet for each reservoir 30, an inlet valve (not shown) for controlling each flow of fluid being drawn into one of the inlets, and a common outlet through which fluid flows from the GPV 28 to one of the pumps 14. A conduit for transporting fluid, for example, a tube, extends from each reservoir 30 to one of the inlets of the GPV 28 and from the outlet of the GPV 28 to the intake side of the pump 14. An example implementation of a gradient proportioning valve is described in U.S. Pat. No. 5,862,832, issued Jan. 26, 1999, the entirety of which patent is incorporated by reference herein.

The gradient controller 24 is in communication with the GPVs 28 to actuate their individual valves sequentially at the appropriate times, thereby managing the intake of fluid from the reservoirs 30 for mixing in desired proportions and producing low-pressure gradient streams 32 over time. From solvent reservoirs 30-1, 30-2, the GPV 28-1 produces low-pressure gradient stream 32-1, and from solvent reservoirs 30-3, 30-4, the GPV 28-2 produces low-pressure gradient stream 32-2. These gradient streams 32 are produced ahead of the pumps 14, and thus under low pressure.

During operation, the pump 14-1 draws and pressurizes the low-pressure gradient stream 32-1 produced by the GPV 28-1, and moves the resulting pressurized low-pressure gradient stream 18-1 to the flow-combining device 20, while the pump 14-2 draws and pressurizes the low-pressure gradient stream 32-2 produced by the GPV 28-2, and moves the resulting pressurized low-pressure gradient stream 18-2 to the flow-combining device 20, where the two pressurized low-pressure gradient streams 18-1, 18-2 combine to produce the pressurized solvent stream 22. Because the flow-combining device 20 is downstream of the pumps 14 the solvent stream 22 is produced at high pressure (e.g., in the range between 5000-15000 psi). As used herein, the phrase "pressurized low-pressure gradient stream" refers to a low-pressure gradient stream that is produced by a GPV and subsequently pressurized to a high pressure by a pump 14.

As an illustration of the operation, consider for example that solvent reservoir 30-1 contains water, solvent reservoir 30-2 contains 1% TFA in water, solvent reservoir 30-3 contains solvent B, and solvent reservoir 30-4 contains 1% TFA in solvent B. To achieve a solvent composition with 0.1% TFA modifier, the gradient controller 24 can control the GPV 28-1 to take a 90% proportion of solvent reservoir 30-1 (water) and a 10% proportion of solvent reservoir 30-2 (1% TFA in water) to produce a low-pressure gradient stream 32-1 of 0.1% TFA in water. In addition, the gradient controller 24 can control the GPV 28-2 to take a 90% proportion of solvent reservoir 30-3 (solvent B) and a 10% proportion of solvent reservoir 30-4 (1% TFA in solvent B) to produce a low-pressure gradient stream 32-2 of 0.1% TFA in solvent B. The pumps 14 draw and pressurize the low-pressure gradient streams 32-1, 32-2, and combine the resulting pressurized low-pressure gradient streams 18-1, 18-2 to produce a pressurized solvent stream 22 comprised of water, solvent B, and 0.1% TFA. The maximum achievable proportion of solvent B is 100%.

In an alternative embodiment, the hybrid solvent delivery system can have one GPV 28 only. For example, consider that GPV 28-2 and the solvents 30-3, 30-4 are not part of the hybrid solvent delivery system 10 shown in FIG. 1, and that the pump 14-2 is instead in direct fluidic communication with a solvent reservoir 30-5. During operation of this embodiment, the pump 14-1 draws and pressurizes the low-pressure gradient stream 32-1 produced by the GPV 28-1, and moves the resulting pressurized low-pressure gradient stream 32-1 to the flow-combining device 20, while the pump 14-2 draws, pressurizes, and moves solvent from reservoir 30-5 to the flow-combining device 20, where the pressurized low-pressure gradient stream 18-1 combines with the solvent 30-5. If the pump 14-2 is turned off, any of the embodiments of the hybrid solvent delivery system 10 can be adapted to operate like a conventional low-pressure gradient system.

Figure 2:
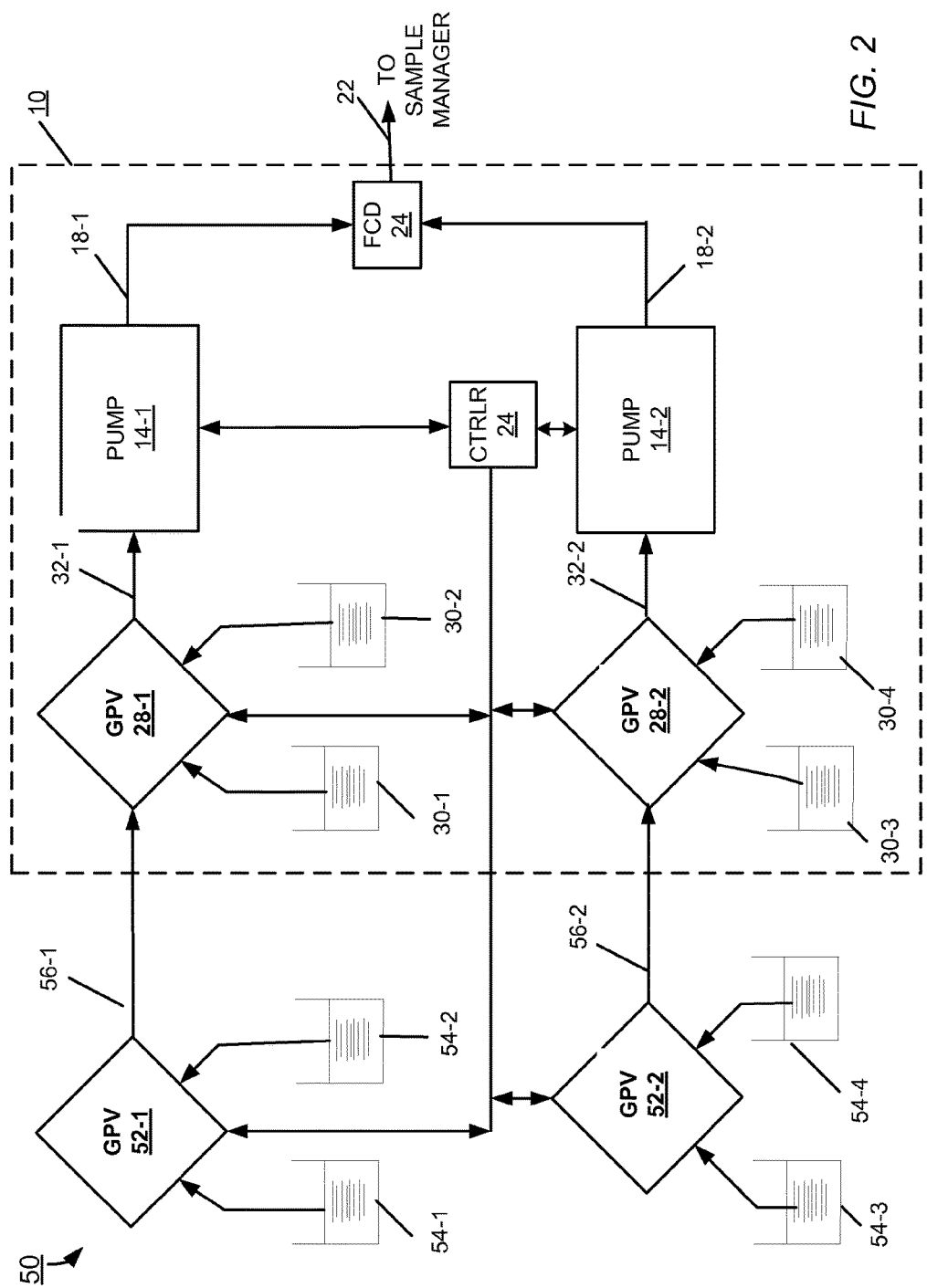
FIG. 2 is a functional block diagram of another embodiment of a hybrid solvent delivery system.

FIG. 2 shows another embodiment of a hybrid solvent delivery system 50, which adds a second stage of GPVs 52 to the hybrid solvent delivery system 10 of FIG. 1. More specifically, the hybrid solvent delivery system 50 includes a GPV 52-1 in fluidic communication with a plurality of solvent reservoirs 54-1, 54-2 and a GPV 52-2 in fluidic communication with a plurality of solvent reservoirs 54-3, 54-4. The outlet of GPV 52-1 is in fluidic communication with one of the inlets of GPV 28-1, while the outlet of GPV 52-2 is in fluidic communication with one of the inlets of GPV 28-2. The gradient controller 24 is in communication with the GPVs 52 to manage the intake of fluid from the reservoirs 54 for mixing in desired proportions and producing low-pressure gradient streams 56-1, 56-2 (generally, 56) over time. From solvent reservoirs 54-1, 54-2, the GPV 52-1 produces low-pressure gradient stream 56-1, and from solvent reservoirs 54-3, 54-4, the GPV 52-2 produces low-pressure gradient stream 56-2.

During operation, the low-pressure gradient stream 32-1 produced by the GPV 28-1 includes a proportion of the low-pressure gradient stream 56-1 produced by the GPV 52-1. The pump 14-1 draws and pressurizes the low-pressure gradient stream 32-1, and moves the resulting pressurized low-pressure gradient stream 18-1 to the flow-combining device 20. Concurrently, the GPV 28-2 produces the low-pressure gradient stream 32-2, which includes a proportion of the low-pressure gradient stream 56-2 produced by the GPV 56-2. The pump 14-2 draws and pressurizes the low-pressure gradient stream 32-2, and moves the resulting pressurized low-pressure gradient stream 18-2 to the flow-combining device 20, where the two pressurized low-pressure gradient streams 18-1, 18-2 combine to produce the pressurized solvent stream 22. In one embodiment, the gradient controller 24 centrally controls the various compositions of each low-pressure gradient stream 32, 56 and the resulting high-pressure gradient stream (i.e., solvent stream 22). In other embodiments, the gradient controller 24 includes a plurality of decentralized controllers that intercommunicate and manage the various compositions in fashion.

In alternative embodiments, the hybrid solvent delivery system 50 can have one second-stage GPV 52 only or one second-stage GPV 52 and one first-stage GPV 28. For example, for one alternative the GPV 52-2 and the solvents 54-3, 54-4 are not part of the hybrid solvent delivery system 50 shown in FIG. 2; in another example alternative, both the GPV 52-2 and GPV 28-2 are not part of the hybrid solvent delivery system 50. Again, if the pump 14-2 is turned off, any of the embodiments of the hybrid solvent delivery system 50 can be adapted to operate like a conventional low-pressure gradient system.

Figure 3:
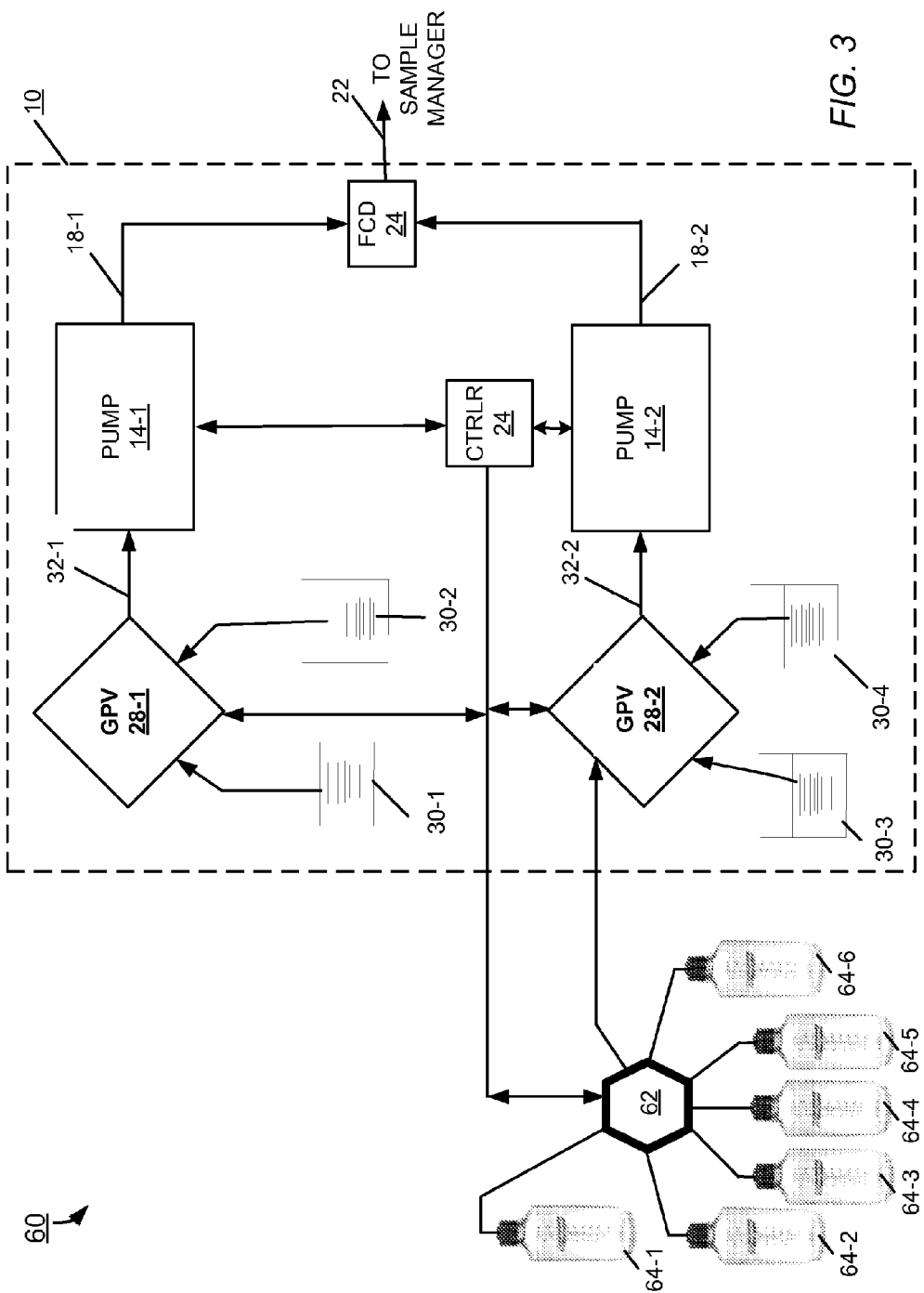
FIG. 3 is a functional block diagram of another embodiment of a hybrid solvent delivery system.

FIG. 3 shows another embodiment of a hybrid solvent delivery system 60, which fluidically connects a switch valve 62 to one of the GPVs 28 of the hybrid solvent delivery system 10 of FIG. 1. More specifically, the hybrid solvent delivery system 60 includes a switch valve 62 in fluidic communication with a plurality of solvent bottles (or reservoirs) 64-1, 64-2, 64-3, 64-4, 64-5, and 64-6. In this example, the outlet of the switch valve 62 is in fluidic communication with one of the inlets of the GPV 28-2. The gradient controller 24 is in communication with the switch valve 62 to select one of the inlets of the switch valve 62, and, thus, the particular solvent bottle 64 from which to draw solvent.

From the solvent drawn through the switch valve 62 and from solvent reservoirs 30-3, 30-4, the GPV 28-2 produces the low-pressure gradient stream 32-2. The pump 14-1 draws and pressurizes the low-pressure gradient stream 32-1 produced by the GPV 28-1 and moves the resulting pressurized low-pressure gradient stream 18-1 to the flow-combining device 20, while the pump 14-2 draws and pressurizes the low-pressure gradient stream 32-2, and moves the resulting pressurized low-pressure gradient stream 18-2, which includes the solvent from the selected solvent bottle 64, to the flow-combining device 20, where the pressurized low-pressure gradient streams 18-1, 18-2 combine.

In like fashion, another switch valve and set of solvent bottles can be fluidically connected to an inlet of the GPV 28-1 instead of or in combination with the switch valve 62 and solvent bottles 64 connected to the GPV 28-2. The embodiments of FIG. 3 are merely illustrative examples of the varying complexity that can be built into a hybrid solvent delivery system.

While the invention has been shown and described with reference to specific preferred embodiments, it should be understood by those skilled in the art that various changes in form and detail may be made therein without departing from the spirit and scope of the invention as defined by the following claims.

What is claimed is:

1. A solvent delivery system for use in a liquid chromatography system, comprising:
    a first gradient proportioning valve in fluidic communication with a first plurality of sources of solvent and producing therefrom a first low-pressure gradient stream;
    a first pump in direct fluidic communication with the first gradient proportioning valve to receive and pressurize the first low-pressure gradient stream and to move the first pressurized low-pressure gradient stream to a flow-combining device;
    a second pump operating in parallel with the first pump, the second pump moving a pressurized solvent stream to the flow-combining device where the pressurized solvent stream combines with the first pressurized low-pressure gradient stream to produce a high-pressure gradient stream;
    a second gradient proportioning valve in direct fluidic communication with an inlet of the first gradient proportioning valve and with a second plurality of sources of solvent, the second gradient proportioning valve producing a second low-pressure gradient stream from the second plurality of sources of solvent, wherein one solvent source of the first plurality of sources of solvent used by the first gradient proportioning valve to produce the first low-pressure gradient stream comprises the second low-pressure gradient stream; and
    a third gradient proportioning valve in fluidic communication with a third plurality of sources of solvent and producing therefrom a third low-pressure gradient stream, and wherein the second pump is in direct fluidic communication with the third gradient proportioning valve to receive and pressurize the third low-pressure gradient stream, wherein the pressurized solvent stream moved by the second pump to the flow-combining device comprises the third low-pressure gradient stream.

2. The solvent delivery system of claim 1, further comprising a fourth gradient proportioning valve in fluidic communication with a fourth plurality of sources of solvent and producing therefrom a fourth low-pressure gradient stream, and wherein the second pump is in fluidic communication with the fourth gradient proportioning valve to receive and pressurize the fourth low-pressure gradient stream, wherein the pressurized solvent stream moved by the second pump to the flow-combining device comprises the pressurized fourth low-pressure gradient stream.

3. The solvent delivery system of claim 1, further comprising:
a fourth gradient proportioning valve in direct fluidic communication with the third gradient proportioning valve and in fluidic communication with a fourth plurality of sources of solvent, the fourth gradient proportioning valve producing a fourth low-pressure gradient stream from the fourth plurality of sources of solvent, wherein one solvent source of the third plurality of sources of solvent used by the third gradient proportioning valve to produce the third low-pressure gradient stream comprises the fourth low-pressure gradient stream.

4. The solvent delivery system of claim 1, further comprising a controller in communication with the first pump, the second pump, and the first gradient proportioning valve, the controller controlling operation of each pump and the first gradient proportioning valve at times to determine a composition of the first low-pressure gradient stream and a composition of the high-pressure gradient stream over time.

5. A solvent delivery system for use in a liquid chromatography system, comprising:
a first gradient proportioning valve having a first valve inlet in direct fluidic communication with a first plurality of sources of solvent and having a first valve outlet in direct fluidic communication with a first pump, the first pump in direct fluidic communication with a flow-combining device;
a second gradient proportioning valve having a second valve outlet in direct fluidic communication with an inlet of the first gradient proportioning valve and a second valve inlet in direct fluidic communication with a second plurality of sources of solvent, the second gradient proportioning valve being in series with the first gradient proportioning valve; and
a third gradient proportioning valve having a third valve inlet in direct fluidic communication with a third plurality of sources of solvent and having a third valve outlet in direct fluidic communication with a second pump, the second pump in direct fluidic communication with the flow-combining device and in parallel with the first pump.

6. The solvent delivery system of claim 5, further comprising a fourth gradient proportioning valve having a fourth valve outlet in direct fluidic communication with the third gradient proportioning valve and a fourth valve inlet in direct fluidic communication with a fourth plurality of sources of solvent, the fourth gradient proportioning valve being in series with the third gradient proportioning valve.

* * * * *